(12) United States Patent
Molnar et al.

(10) Patent No.: US 9,357,905 B2
(45) Date of Patent: Jun. 7, 2016

(54) AIRWAY DEVICE, AIRWAY ASSIST DEVICE AND THE METHOD OF USING SAME

(76) Inventors: Robert Molnar, Long Grove, IL (US); Arcangelo Michele Iusco, Des Plaines, IL (US)

( * ) Notice: Subject to any disclaimer, the term of this patent is extended or adjusted under 35 U.S.C. 154(b) by 838 days.

(21) Appl. No.: 13/486,549

(22) Filed: Jun. 1, 2012

(65) Prior Publication Data

US 2013/0324798 A1    Dec. 5, 2013

(51) Int. Cl.
| | |
|---|---|
| A61M 16/04 | (2006.01) |
| A61B 1/04 | (2006.01) |
| A61B 1/05 | (2006.01) |
| A61B 1/06 | (2006.01) |
| A61B 1/267 | (2006.01) |

(52) U.S. Cl.
CPC ............. *A61B 1/05* (2013.01); *A61B 1/0676* (2013.01); *A61B 1/0684* (2013.01); *A61B 1/267* (2013.01); *A61M 16/04* (2013.01); *A61M 16/042* (2014.02); *A61M 16/0409* (2014.02); *A61M 16/0463* (2013.01); *A61M 16/0488* (2013.01); *A61M 2205/3375* (2013.01); *A61M 2205/502* (2013.01); *A61M 2230/04* (2013.01)

(58) Field of Classification Search
CPC ............ A61M 16/04; A61M 16/0409; A61M 16/042; A61M 16/0434; A61M 16/0463; A61M 16/0486; A61M 16/0488; A61M 2025/0037; A61M 25/0113; A61M 2205/3375; A61M 2230/04; A61B 1/00089; A61B 1/00154; A61B 1/042; A61B 1/05; A61B 1/0676; A61B 1/0684; A61B 1/267
USPC ........................ 128/200.26, 207.14–207.17; 604/103.03; 606/108
See application file for complete search history.

(56) References Cited

U.S. PATENT DOCUMENTS

| | | | |
|---|---|---|---|
| 4,360,008 A | 11/1982 | Corazzelli | |
| 4,584,998 A | 4/1986 | McGrail | |
| 4,607,643 A * | 8/1986 | Bell | A61B 7/023 128/207.15 |

(Continued)

FOREIGN PATENT DOCUMENTS

| | | |
|---|---|---|
| WO | 03/084719 A2 | 10/2003 |
| WO | 2009025843 A1 | 2/2009 |

(Continued)

OTHER PUBLICATIONS http://worldnetdaily.co.uk/markets/news/read/20671060/etview_medical.

(Continued)

*Primary Examiner* — Tan-Uyen (Jackie) T Ho
*Assistant Examiner* — Joseph D Boecker
(74) *Attorney, Agent, or Firm* — Klintworth & Rozenblat IP LLC

(57) ABSTRACT

An airway device is provided for opening a patient's airway. The airway device provides dual tubes which allow the patient to breathe on his/her own, to be ventilated, or to be intubated. The airway device includes a camera which provides constant visualization of the patient's tissues during insertion of the airway device and during the entire medical procedure. A transmission lumen monitors heart and breath sounds. Information from the camera and the transmission lumen is relayed to a microprocessor to allow for monitoring which may be remote. An airway assist device may be used with the airway device for properly positioning the patient's tongue is also disclosed. The airway assist device is inserted into the patient's vallecula to manipulate the patient's tongue.

21 Claims, 12 Drawing Sheets

(56) References Cited

U.S. PATENT DOCUMENTS

| | | | |
|---|---|---|---|
| 5,193,692 A | 3/1993 | Farley et al. | |
| 5,241,956 A * | 9/1993 | Brain | A61M 16/0463 128/207.14 |
| 5,353,787 A * | 10/1994 | Price | A61M 16/04 128/200.26 |
| 5,511,916 A | 4/1996 | Farley et al. | |
| 5,513,627 A * | 5/1996 | Flam | A61M 16/0488 128/200.26 |
| 5,632,271 A * | 5/1997 | Brain | A61M 16/04 128/207.14 |
| 5,682,880 A * | 11/1997 | Brain | A61M 16/0409 128/200.26 |
| 5,740,791 A * | 4/1998 | Aves | A61B 1/32 128/200.26 |
| 5,819,733 A | 10/1998 | Bertram | |
| 5,888,195 A * | 3/1999 | Schneider | A61B 1/267 600/191 |
| 6,142,144 A | 11/2000 | Pacey | |
| 6,189,533 B1 | 2/2001 | Simon et al. | |
| 6,386,199 B1 * | 5/2002 | Alfery | A61M 16/04 128/200.26 |
| 6,439,232 B1 * | 8/2002 | Brain | A61M 16/04 128/200.26 |
| 6,440,061 B1 * | 8/2002 | Wenner | A61B 1/3132 600/114 |
| 6,443,156 B1 | 9/2002 | Niklason et al. | |
| 6,543,447 B2 | 4/2003 | Pacey | |
| 6,626,169 B2 | 9/2003 | Gaitini | |
| 6,631,720 B1 * | 10/2003 | Brain | A61M 16/04 128/207.14 |
| 6,634,354 B2 * | 10/2003 | Christopher | A61M 16/0488 128/200.26 |
| 6,655,377 B2 | 12/2003 | Pacey | |
| 7,052,456 B2 | 5/2006 | Simon | |
| 7,128,509 B2 | 10/2006 | Farley et al. | |
| 7,156,091 B2 | 1/2007 | Koyama et al. | |
| 7,237,993 B2 | 7/2007 | Farley et al. | |
| 7,331,925 B2 | 2/2008 | McMorrow et al. | |
| 7,450,746 B2 | 11/2008 | Yang et al. | |
| 7,520,857 B2 | 4/2009 | Chalana et al. | |
| 7,527,601 B2 | 5/2009 | Dubey et al. | |
| 7,611,466 B2 | 11/2009 | Chalana et al. | |
| 7,654,970 B2 | 2/2010 | Dubey | |
| 7,713,216 B2 | 5/2010 | Dubey et al. | |
| 7,727,150 B2 | 6/2010 | Chalana et al. | |
| 7,744,534 B2 | 6/2010 | Chalana et al. | |
| 7,749,165 B2 | 7/2010 | McMorrow et al. | |
| 7,749,176 B2 | 7/2010 | Dubey | |
| 7,811,239 B2 | 10/2010 | Dubey et al. | |
| 7,819,806 B2 | 10/2010 | Yang et al. | |
| 7,854,324 B2 | 12/2010 | Farley et al. | |
| 7,896,007 B2 | 3/2011 | Brain | |
| 7,976,458 B2 * | 7/2011 | Stefanchik | A61B 10/00073 600/104 |
| 8,016,760 B2 | 9/2011 | Chalana et al. | |
| 8,202,215 B2 * | 6/2012 | Xiao | A61B 1/00105 600/120 |
| 8,215,307 B2 * | 7/2012 | Nasir | A61M 16/04 128/200.26 |
| 8,297,275 B2 * | 10/2012 | Ogilvie | A61M 16/0488 128/200.24 |
| 8,529,442 B2 * | 9/2013 | Pacey | A61B 1/00142 600/187 |
| 2005/0182297 A1 | 8/2005 | Gravenstein et al. | |
| 2006/0111633 A1 | 5/2006 | McMorrow et al. | |
| 2006/0162730 A1 | 7/2006 | Glassenberg et al. | |
| 2006/0180155 A1 | 8/2006 | Glassenberg et al. | |
| 2006/0276694 A1 * | 12/2006 | Acha Gandarias | A61B 1/015 600/194 |
| 2007/0137651 A1 | 6/2007 | Glassenberg et al. | |
| 2007/0156068 A1 | 7/2007 | Dubey | |
| 2007/0180887 A1 | 8/2007 | Frenken | |
| 2007/0203393 A1 * | 8/2007 | Stefanchik | A61B 1/00073 600/106 |
| 2007/0239197 A1 | 10/2007 | Dubey | |
| 2007/0255185 A1 | 11/2007 | Dubey | |
| 2008/0029100 A1 | 2/2008 | Glassenberg et al. | |
| 2008/0114268 A1 | 5/2008 | Dubey | |
| 2008/0146879 A1 | 6/2008 | Pacey | |
| 2008/0188774 A1 | 8/2008 | Dubey | |
| 2008/0276932 A1 * | 11/2008 | Bassoul | A61M 16/04 128/200.26 |
| 2009/0194114 A1 * | 8/2009 | Chen | A61M 16/04 128/207.15 |
| 2010/0249639 A1 | 9/2010 | Bhatt | |
| 2010/0261967 A1 * | 10/2010 | Pacey | A61B 1/00103 600/186 |
| 2011/0030694 A1 | 2/2011 | Schaner et al. | |
| 2011/0178372 A1 * | 7/2011 | Pacey | A61B 1/267 600/188 |
| 2011/0201882 A1 | 8/2011 | Schwartz et al. | |
| 2011/0315147 A1 * | 12/2011 | Wood | A61M 16/0486 128/207.15 |
| 2012/0259173 A1 * | 10/2012 | Waldron | A61B 1/00073 600/109 |
| 2012/0260921 A1 | 10/2012 | Sangwan | |
| 2013/0030249 A1 | 1/2013 | Vazales et al. | |
| 2014/0194694 A1 * | 7/2014 | Chen | A61B 1/053 600/188 |

FOREIGN PATENT DOCUMENTS

| | | |
|---|---|---|
| WO | 2012/080293 A2 | 6/2012 |
| WO | 2013/017535 A2 | 2/2013 |

OTHER PUBLICATIONS http://www.cardiomed.com/products/anesthesiology?task=callelement&format=raw&item__id=113&element=be8726ed-4912-4242-951f-765db1f52b3f&method=download.
http://www.etview.com/index__old.php.
http://www.etview.com/sites/all/themes/etview/docs/ETV__A16703__ETView__Brochure.pdf.
http://finance.yahoo.com/news/etview-medical-ltd-announces-appointment-104300770.html.
http://www.aja-online.com/fileadmin/user__upload/Edition__pdfs/2011/Vol-12__1-2011/03.__22-33__Laryngeal__tube__a__review__of__current__literature.pdf.
How to Use a JEM Endotracheal Tube Changer, 2 pages.
http://www.jems.com/article/patient-care/intubation-threatened-new-devi.
http://www.capnography.com/outside/911.htm.
http://www.bryanbledsoe.com/data/pdf/handouts/PowerPoint/Future%20of%20Intubation.pptx.
http://www.cardiomed.com/products/anesthesiology?task=callelement&format=raw&item  id=113&element=be8726ed-4912-4242-951f-765db1f52b3f&method=download.
How to use a JEM Endotracheal Tube Changer.

\* cited by examiner

AIRWAY DEVICE, AIRWAY ASSIST DEVICE AND THE METHOD OF USING SAME

FIELD OF THE INVENTION

The present invention relates to an airway device for allowing a patient to breathe on his/her own, to be ventilated, or to be intubated, and its method of use, and relates to an airway assist device used with the airway device for properly positioning the tongue of a patient and its method of use.

BACKGROUND OF THE INVENTION

Laryngeal mask airways are known in the art. A laryngeal mask airway is used to ventilate and to supply anesthetic to a patient during surgery. A laryngeal mask airway is different than an endotracheal tube in that the laryngeal mask airway is positioned in the throat of the patient proximally of the vocal folds, while an endotracheal tube is passed through the vocal folds and is positioned in the patient's trachea.

Laryngeal mask airways of the prior art generally have a tube opening into the center of a generally elliptical dome. The tube is generally straight, but can flex to assume a curved shape. A cuff, which may be inflatable, is sometimes attached to the perimeter of the dome.

In use, the medical professional inserts the laryngeal mask airway into the mouth of the patient. The open tube allows the patient to breathe on his/her own during insertion. The tube can also be connected to a ventilator to provide assisted breathing to the patient. For insertion, the cuff (if provided), the dome and the tube slide against the hard palate and then against the soft palate and into the pharynx of the patient. This procedure is performed blindly and only by feel which comes from experience in performing the procedure. Trauma to the patient may occur when placing the laryngeal mask airway as a result of the laryngeal mask airway attempting to conform to a curved position in the pharynx. When properly positioned in the hypo-pharynx, the proximal end of the cuff seats against the epiglottis pushing it toward the tongue of the patient and the distal end of the cuff seats in the esophagus. At times, the cuff may be positioned such that the epiglottis is pushed downwardly and may at least partially block the tube opening. This is not a desirable result as the blocking by the epiglottis can cause problems with the airflow through the laryngeal mask airway. In addition, inappropriate sizing and differences in the anatomy of patients may also impair the proper positioning of the laryngeal mask airway. Since the insertion is performed blindly, the medical professional will not know if proper placement of the laryngeal mask airway has occurred. After positioning the laryngeal mask airway, the inflatable cuff (if provided) is inflated and the patient's esophagus is blocked by the cuff. The medical professional will listen for breath sounds and ascertain end tidal $CO_2$ gases from the patient to verify proper positioning of the laryngeal mask airway.

If the medical professional needs to insert an endotracheal tube into the patient, the endotracheal tube can be inserted through the tube of the laryngeal mask airway to intubate the patient. If the epiglottis is at least partially blocking the opening in the tube, this intubation may be difficult. In addition, the glottis opening quite often does not align with the tube opening which can make this blind insertion difficult and may result in trauma to the laryngeal inlet.

An airway device is provided herein which provides improvements to existing laryngeal mask airways and which overcomes the disadvantages presented by the prior art. Other features and advantages will become apparent upon a reading of the attached specification, in combination with a study of the drawings.

SUMMARY OF THE INVENTION

An airway device, an airway assist device and their method of use are disclosed. The airway device is used to open the airway of a patient. The airway device provides dual tubes which allow the patient to breathe on his/her own, to be ventilated by a medical professional, or to be intubated by a medical professional. The airway device includes a camera which provides constant visualization of the tissues of the patient during insertion of the airway device into the patient and during the entire medical procedure. A transmission lumen monitors heart and breath sounds. Information from the camera and the transmission lumen is relayed to a microprocessor to allow for monitoring which may be remote. The airway assist device is used with the airway device for properly positioning the tongue of a patient prior to final seating of the airway device in the throat of the patient. The airway assist device is inserted into the vallecula of the patient and manipulated to move the tongue and thus the epiglottis of the patient to a desired position.

BRIEF DESCRIPTION OF THE DRAWINGS

The organization and manner of the structure and operation of the invention, together with further objects and advantages thereof, may best be understood by reference to the following description, taken in connection with the accompanying drawings, wherein like reference numerals identify like elements in which.

DETAILED DESCRIPTION OF THE ILLUSTRATED EMBODIMENTS

Figure 1:
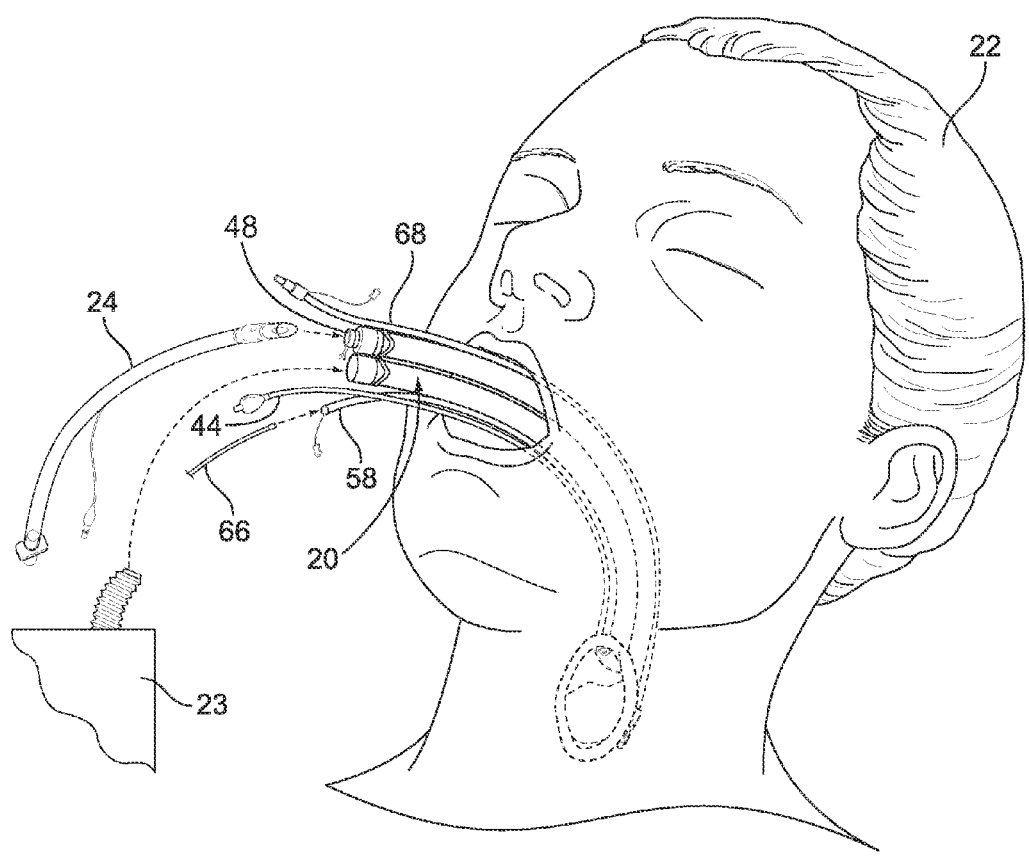
FIG. 1 is a perspective view of an airway device inserted into a patient, and shown with an endotracheal tube and a ventilator which are capable of being used with the airway device.
Figure 2:
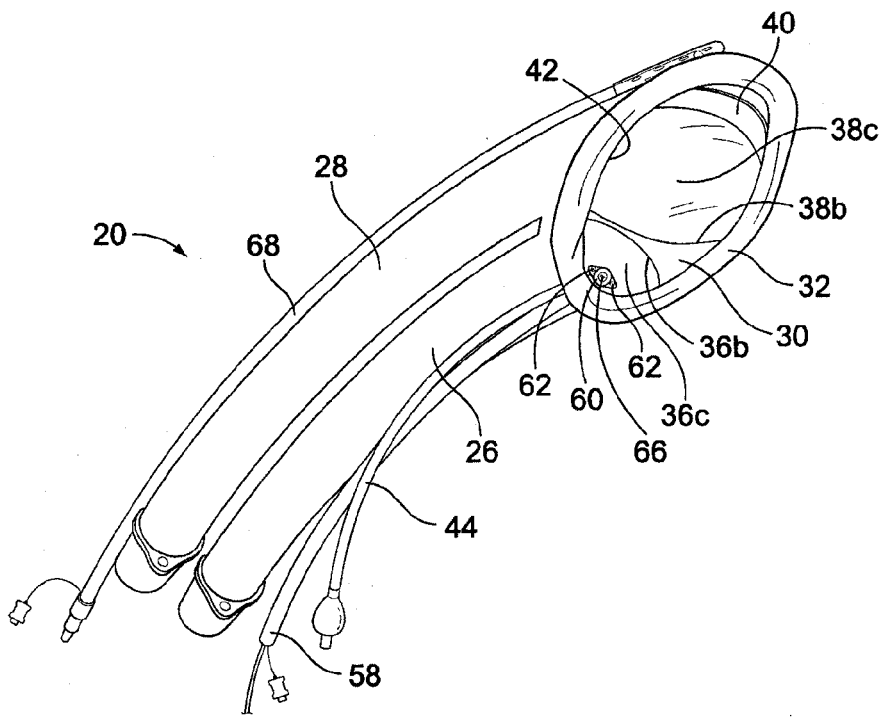
FIG. 2 is a perspective view of the airway device.
Figure 3:
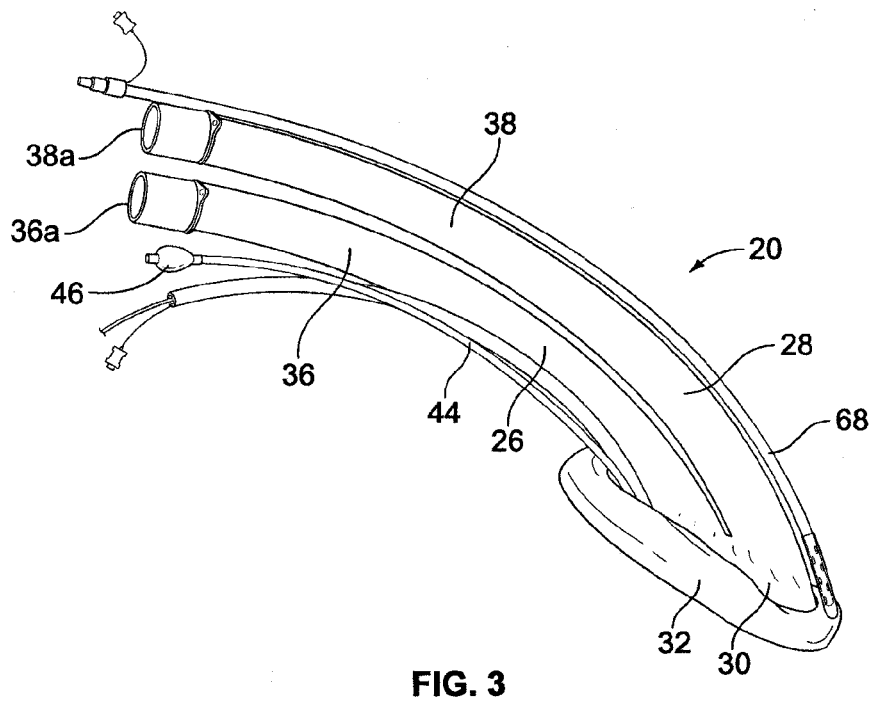
FIG. 3 is an alternate perspective view of the airway device.
Figure 4:
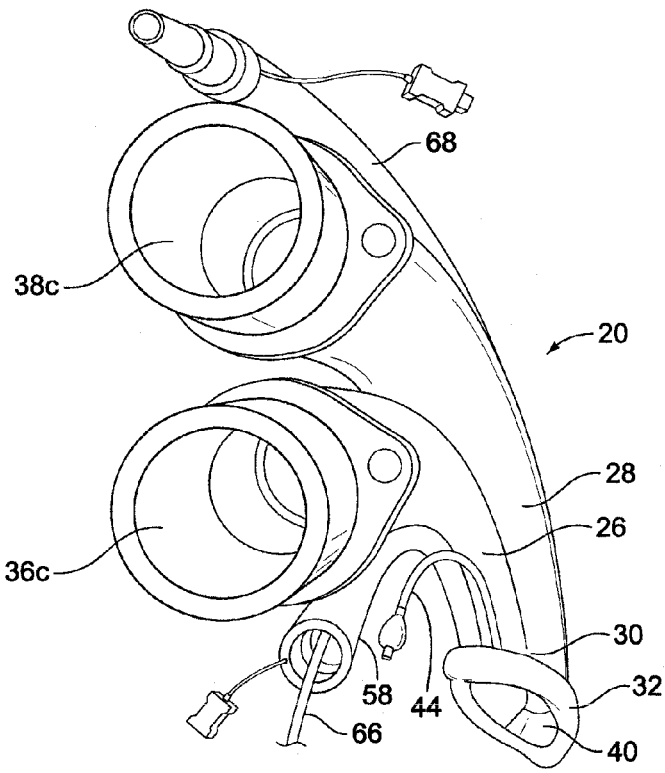
FIG. 4 is yet another alternate perspective view of the airway device.
Figure 5:
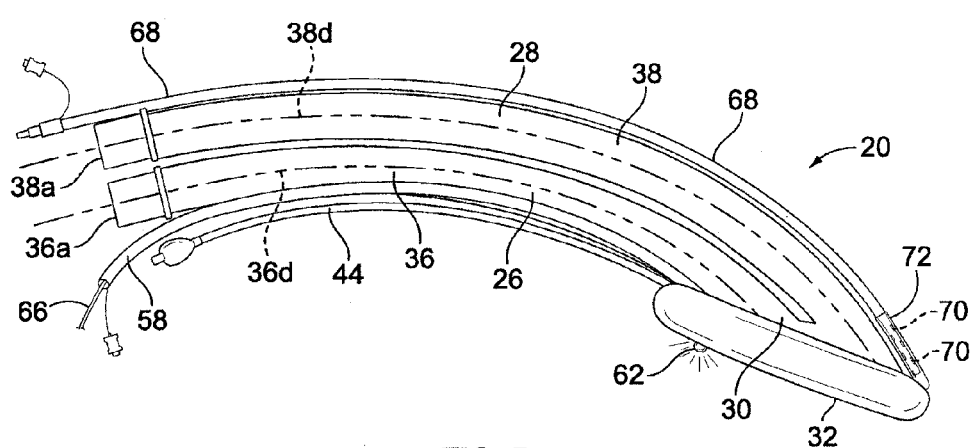
FIG. 5 is a side elevational view of the airway device.
Figure 6:
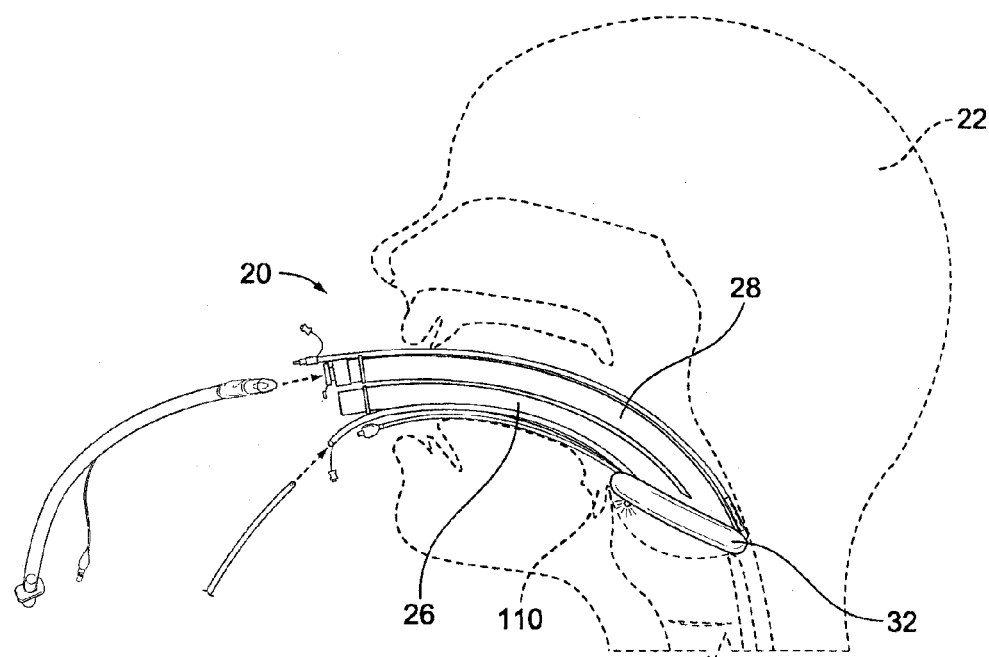
FIG. 6 is a side elevational view of the airway device inserted into a patient.
Figure 7:
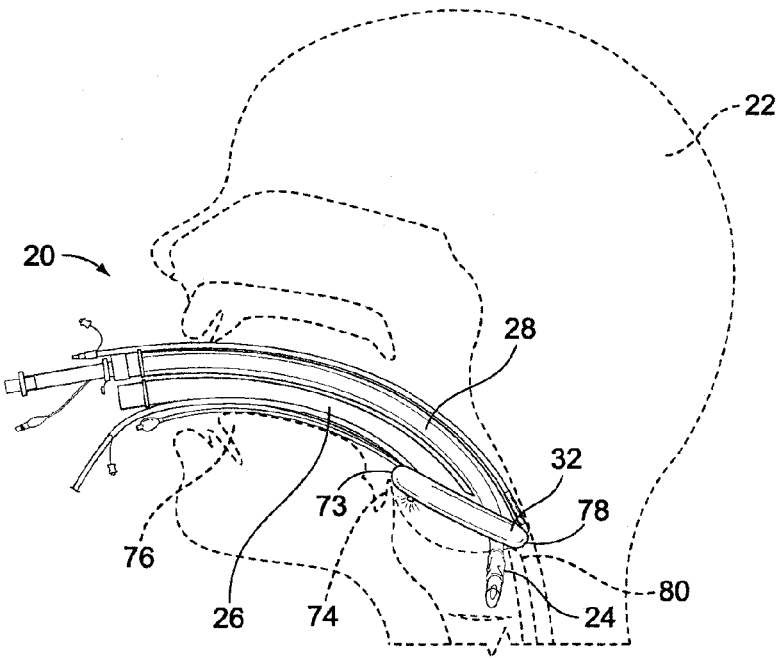
FIG. 7 is a side elevational view of the airway device inserted into a patient, and shown with an endotracheal tube inserted therein.

While the invention may be susceptible to embodiment in different forms, there is shown in the drawings, and herein will be described in detail, a specific embodiment with the understanding that the present disclosure is to be considered an exemplification of the principles of the invention, and is not intended to limit the invention to that as illustrated and described herein. Therefore, unless otherwise noted, features disclosed herein may be combined together to form additional combinations that were not otherwise shown for purposes of brevity.

Figure 8:
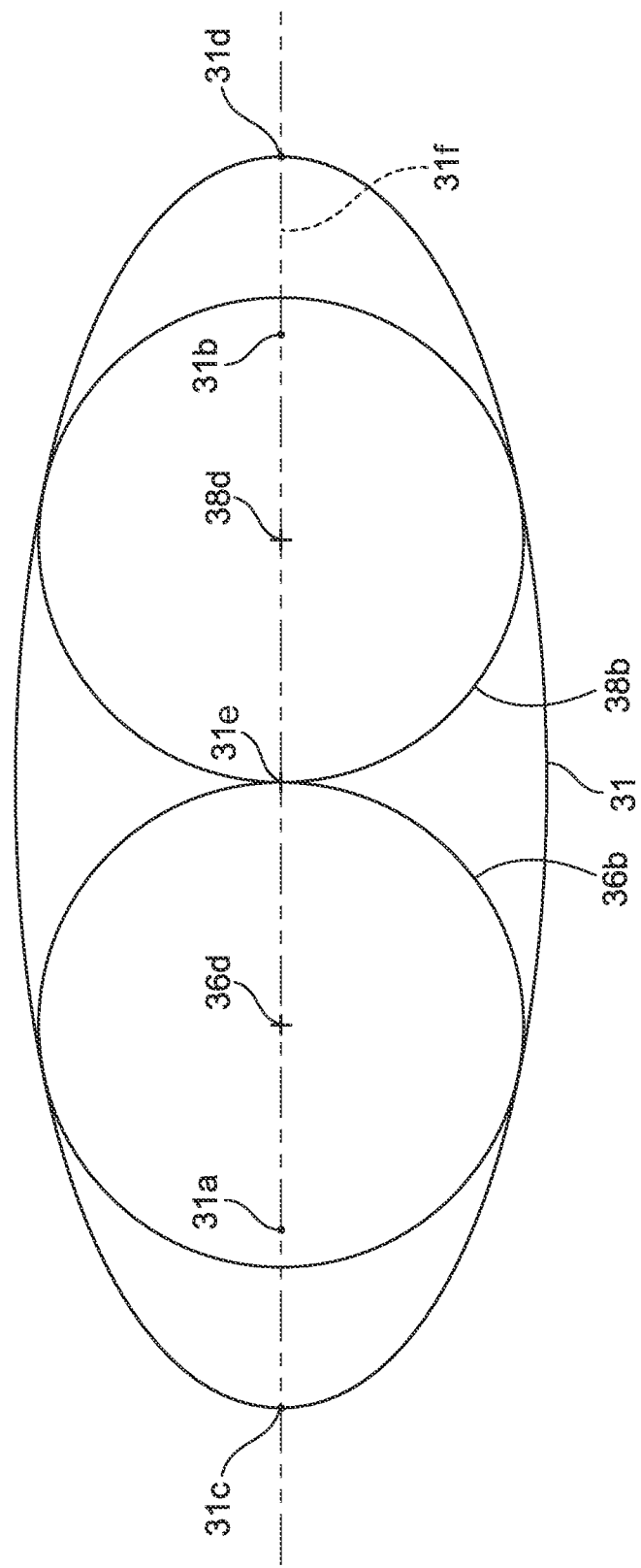
FIG. 8 is a schematic view of the airway device.
Figure 9:
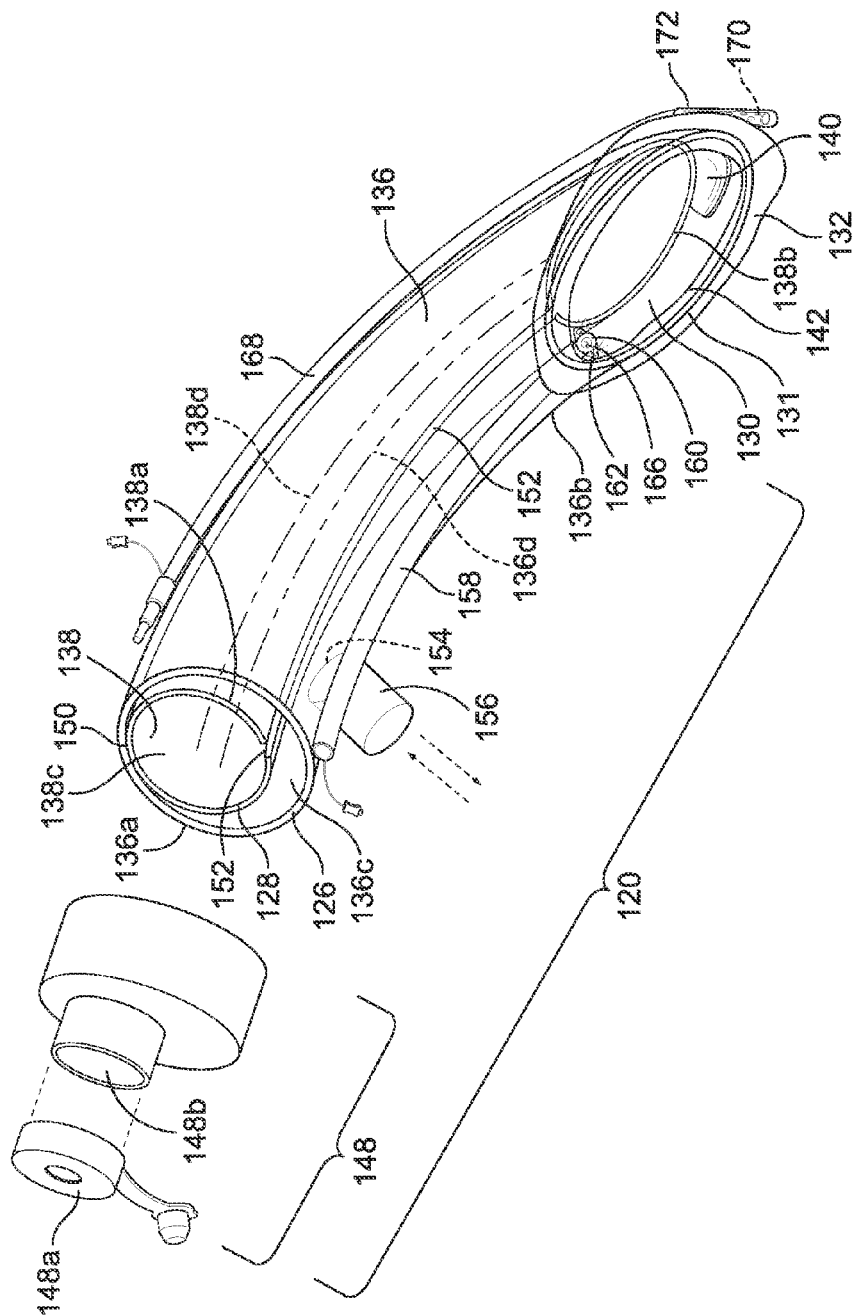
FIG. 9 is a perspective view of an alternate airway device.

FIGS. 1-8 show a first embodiment of an airway device 20 and FIGS. 9/9A and 10 show a second embodiment of an airway device 120. The airway device 20, 120 is inserted into the throat of a patient 22 to open the airway to allow the patient 22 to breathe on his/her own, to allow the patient 22 to breathe with ventilation via a ventilator 23 or for intubating the patient 22 with an endotracheal tube 24. Each airway device 20, 120 is formed of a dual-tube design which includes a ventilating tube 26, 126 and an intubating tube 28, 128 which are connected to a dome 30, 130. A cuff 32, 132, which may inflatable, is attached to the perimeter 31, 131 of the dome 30, 130. While the inflatable cuff 32, 132 is shown and described herein, the inflatable cuff 32, 132 is not necessary and may be formed of rubber provided at the end of the tubes 26, 126, 28, 128. The dual-tube design provides the ventilating tube 26, 126 for allowing the patient to breathe on his/her own or for ventilation, and the intubating tube 28, 128 for intubation of the patient 22.

Attention is invited to the first embodiment of the airway device 20 shown in FIGS. 1-8.

Each tube 26, 28 is formed from a cylindrical wall 36, 38 having a proximal open inlet 36a, 38a (at the end closest to the medical professional), an opposite distal open outlet 36b, 38b (at the end furthest away from the medical professional during use of the airway device 20) and a central passageway 36c, 38c extending through the respective tube 36, 38. Each tube 36, 38 has a centerline 36d, 38d which extends from the proximal inlet 36a, 38a to the distal outlet 36b, 38b. The tubes 26, 28 are curved along the length of each tube 26, 28 and the centerlines 36d, 38d are accordingly curved. Each tube 26, 28 has a diameter which is preferably 15 mm, however, each tube 26, 28 may be bigger or smaller, and/or not of equal diameter with respect to each other. Each tube 26, 28 is formed of a relatively stiff but compliant plastics material and is preferably formed by extrusion. The tubes 26, 28 are situated side-by-side and thus the centerlines 36d, 38d of the tubes 26, 28 are parallel to each other. The inlets 36a, 38a generally align with each other, and the outlets 36b, 38b generally align with each other. Proximate to the distal outlets 36b, 38b of the tubes 26, 28, the inner portions of the walls 36, 38 merge together at the dome 30.

The dome 30 is formed of a plastics material like that of the tubes 26, 28. The dome 30 has a ramped surface 40 proximate to the intubating tube 28 which acts as a ramp for the insertion of the endotracheal tube 24 into the throat of the patient 22. The perimeter 31 of the dome 30 distal from the distal ends of the tubes 26, 28 generally forms an ellipse.

The centerlines 36d, 38d of the tubes 26, 28 generally fall along the major axis 31f of the ellipse and are offset from each other, with one centerline 36d proximate to one focus 31a of the ellipse and the other centerline 38d proximate to the other focus 31b of the ellipse. As schematically shown in FIG. 8, the distal open outlet 36b of the ventilating tube 26 generally aligns with focus 31a and forms a ventilating passageway. The distal open outlet 38b of the intubating tube 28 generally aligns with focus 31b. The ramped surface 40 is between distal open outlet 38b of the intubating tube 28 and the vertex 31d of the ellipse. The inner portions of the walls 36, 38 preferably generally align with the center 31c of the ellipse. The intubating tube 28 and the ramped surface 40 form an intubating passageway along their lengths. While the distal open outlet 38b of the intubating tube 28 is described and shown as generally aligning with focus 31b, it is to be understood that the ramped surface 40 can be positioned to generally align with this focus 31b.

The inflatable cuff 32 surrounds the perimeter 31 of the dome 30. A central opening 42 is formed by the cuff 32. The inner edge of the cuff 32 is bonded or otherwise suitably secured, such as by ultrasonic welding, to the perimeter 31 of the dome 30. Thus the inner edge of the cuff 32 is generally elliptical. The cuff 32 is preferably formed of a thin, flexible plastics material so that the cuff 32 can be deflated to a low profile for insertion into the patient 22 and can be inflated to seal with the surrounding tissue when the airway device 20 is correctly positioned in the throat of the patient 22 as described herein.

The airway device 20 includes an inflation line 44 which is formed by a small-diameter flexible plastic tube. As shown, the inflation line 44 is provided proximate to the ventilating tube 26 at a position farthest from the intubating tube 28. This position is only illustrative and the inflation line 44 can be provided at other locations. The distal end of the inflatable cuff 32 is sealed with the outside of the inflation line 44 so that it opens into the interior of the inflatable cuff 32. The proximal end of the inflation line 44 is attached to a combined inflation indicator balloon and connector 46 which are known in the art. The inflation line 44 can be attached to one of the tubes 26, 28 along its length, if desired. Alternatively, an extruded small-bore lumen (not shown) can be provided within the wall 36, 38 of one of the tubes 26, 28 to provide the inflation line 44.

A cap 48 is provided at the proximal end of the intubating tube 28 for sealing the proximal outlet 38a of the intubating tube 28 when it is not in use. Preferably, the cap 48 is formed of rubber. The cap 48 can have a flip-top, or can be removed from the intubating tube 28, to allow access to the intubating passageway when needed. Other means for sealing the end of the intubating tube 28, while selectively allowing access to the intubating passageway therein, are within the scope of the present invention.

The airway device 20 includes a camera lumen 58 which is formed by a small-diameter flexible plastic tube. The camera lumen 58 has a distal end which is preferably provided at the vertex 31e of the ellipse between the ventilating tube 26 and the cuff 32. The ventilating tube 26 and the cuff 32 are sealed to the camera lumen 58 by suitable means. A clear window 60 is provided at the distal end of the camera lumen 58 and is sealed to the camera lumen 58. A pair of LED lights 62 are formed in the wall of the camera lumen 58 on opposite sides of the window 60. Wires are molded into the camera lumen 58 and extend from the proximal end thereof for connection to a suitable power source. A camera 66 can be easily slid into and removed from the sealed camera lumen 58. Alternatively, an extruded small-bore lumen can be provided within the wall of the ventilating tube 26, with the window 60 sealed to the end thereof. The camera 66 and LED lights 62 (or other source of lighting, including a camera with its own built-in lighting) can be incorporated into a single device which is insertable and removeable from the camera lumen 58 or small-bore lumen. The camera 66 is preferably provided at the vertex 31e of the ellipse between the ventilating tube 26 and the cuff 32 as this provides the best angle for viewing the tissues of the patient 22 when the airway device 20 is being inserted. It is to be understood that the camera 66 can be placed in other positions.

The airway device 20 includes a transmission lumen 68 for transmitting breath and heartbeat sounds from the patient 22 to the medical professional. The transmission lumen 68 is formed by a small-diameter flexible plastic tube which has a series of perforations 70 at its distal end. The perforations 70 are covered by a thin gauge plastic cap 72. The transmission lumen 68 seats against the intubating tube 28 and the distal end of the transmission lumen 68 is attached to the cuff 32 or is attached near the distal outlet 38b of the ventilating tube 26 near the cuff 32, such that the end of the transmission lumen 68 is positioned proximate to the ramped surface 40. When the airway device 20 is seated in the throat of the patient 22, the distal end of the transmission lumen 68 is positioned closest to the esophagus which enables breath and heartbeat sounds to be easily transmitted through the perforations 70 and along the length of the transmission lumen 68 to the medical professional monitoring the patient 22.

In use, the medical professional inserts the airway device 20 through the mouth and into the throat of the patient 22. The intubating tube 28 is closed by the cap 48 at its proximal outlet 38a and is not used. The ventilating tube 26 remains open to allow the patient 22 to breathe on his/her own through the ventilating tube 26 through the open proximal inlet 36a of the ventilating tube 26. The ventilating tube 26 can also be connected to the ventilator 23 to provide assisted breathing to the patient 22. The cuff 32 and the intubating tube 28 slide against the hard palate and then against the soft palate and into the pharynx of the patient 22. The airway device 20 will flex to assume a curved shape to conform to the throat of the patient 22. The medical professional uses the camera 66 to properly guide the airway device 20 into the pharynx. Because the camera 66 provides constant visualization of the tissues during insertion of the airway device 20 into the patient, the medical professional can be assured that the airway device 20 is being properly inserted and positioned in the throat of the patient 22 with limited trauma to the patient 22. The medical professional can see the vocal folds via the camera 66 to ensure proper positioning of the airway device 20 in the patient's throat. Once positioned in the pharynx, one end 73 of the cuff 32 seats against the epiglottis 74 pushing it toward the tongue 76 of the patient 22 and the opposite end 78 of the cuff 32 seats in the esophagus 80. The cuff 32 is then inflated. As a result, the esophagus 80 is blocked by the cuff 32 and the epiglottis 74 is moved out of the way of the ventilating and intubating passageways 36c, 38c. The distal outlets 36b, 38b of the ventilating and intubating passageways 36c, 38c are open to the glottis of the patient 22. During this entire procedure of insertion, the camera 66 provides constant visualization of the tissues during insertion of the airway device 20 into the patient 22. The patient 22 can breathe by airflow through the open ventilating tube 26. Since the camera 66 is constantly operating during insertion and through the entire medical procedure, the medical professional can constantly visually confirm that the patient 22 is breathing. The constant visualization of the laryngeal inlet and the vocal folds of the patient 22 can make earlier diagnoses of issues, for example, but not limited to, secretions, tumors, paralyzed vocal folds, apnea, bleeding, and abnormal anatomy, as well as other potentially harmful effects to the patient 22.

If the medical professional needs to insert an endotracheal tube 24 into the patient 22, the cap 48 on the intubating tube 28 is removed/opened and the endotracheal tube 24 is inserted through the proximal outlet 38a of the intubating tube 28 and through the passageway 38c of the intubating tube 28. The endotracheal tube 24 will contact the ramped surface 40 which properly directs the endotracheal tube 24 into the pharynx. Once the endotracheal tube 24 exits the intubating tube 28 at its distal outlet 38b, the medical professional can see the positioning of the endotracheal tube 24 via the camera 66. The medical professional can thus guide the endotracheal tube 24 through the vocal folds and into the trachea, and inflate the cuff of the endotracheal tube 24, under the constant visualization provided by the camera 66. At times, the airway device 20 may be advanced, pulled back, or turned from side to side, to maintain the proper trajectory through the vocal folds. This is easily accomplished since there is constant visualization of the tissues via the camera 66. In addition, known moveable stylettes (not shown) may be used. The ventilator 23 is then disconnected from the ventilating tube 26 and the ventilating tube 26 is capped, or the ventilator 23 remains connected, but turned off.

As a result of the structure of the medical device 20, the intubating tube 28 is located furthest away from the epiglottis 74 when the airway device 20 is positioned within the patient 22. This minimizes the ability of the epiglottis 74 to block the insertion of the endotracheal tube 24 into the trachea in the event that the epiglottis 74 is not seated between the cuff 32 and the tongue 76.

Figure 10:
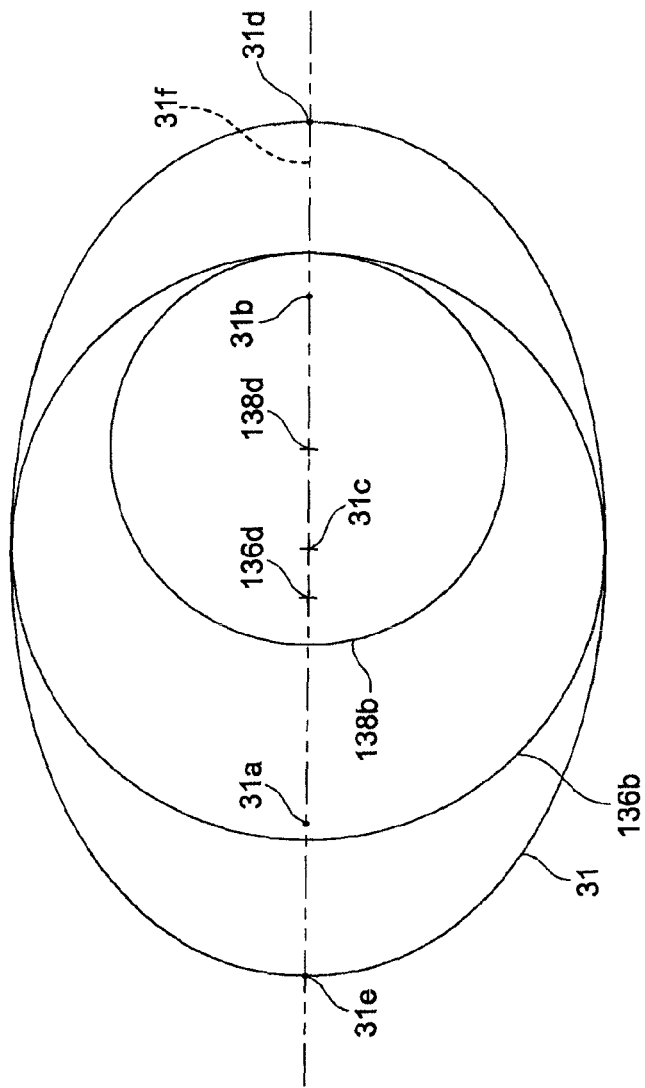
FIG. 10 is a schematic view of the airway device of FIG. 9.

Attention is now invited to the second embodiment of the airway device 120 shown in FIGS. 9 and 10. Each tube 126, 128 is formed from a cylindrical wall 136, 138 having a proximal open inlet 136a, 138a (at the ends closest to the medical professional), an opposite open distal outlet 136b, 138b (at the ends furthest away from the medical professional during use of the airway device 120) and a central passageway 136c, 138c extending through the respective tube 126, 128. Tube 128 is shown in full line in FIG. 9 to illustrate the construction of the tube 128 (of course, in practice, tube 126 may be opaque such that tube 128 would not be visible along its length). The outlets 136b, 138b generally align with each other. Each tube 126, 128 has a centerline 136d, 138d which extends from the proximal inlet 136a, 138a to the distal outlet 136b, 138b. The tubes 126, 128 are curved along the lengths thereof and the centerlines 136d, 138d are accordingly curved. Each tube 126, 128 is formed of a relatively stiff but compliant plastics material and is preferably formed by extrusion. Tube 126 forms the ventilating tube, however, tube 128 is also used in the ventilating process as described herein. Tube 128 forms the intubating tube.

The intubating tube 128 is positioned within the ventilating tube 126. A portion of the wall 136 of the ventilating tube 126 is preferably connected to the intubating tube 128, as shown in FIG. 9, along a junction 150 to affix the tubes 126, 128 together and to prevent the intubating tube 128 from moving around within the ventilating tube 126. The centerlines of the tubes 126, 128 are parallel to each other. The ventilating tube 126 has a diameter which is preferably 20 mm, and the intubating tube 128 has a diameter which is preferably 10 mm.

The intubating tube 128 has an elongated slit 152 along its length opposite to the junction 150 to allow for gas communication between the passageway 136c of the ventilating tube 126 and the passageway 138c of the intubating tube 128. The slit 152 can extend the entire length of the intubating tube 128 as shown, or can extend along a portion of the length of the intubating tube 128.

The ventilating tube 126 has a ventilating port 154 in its wall 136 proximate to, but spaced from, the proximal open inlet 136a thereof. The ventilating port 154 is preferably proximate to the slit 152 in the intubating tube 128. A connector tube 156 is formed around the ventilating port 154. The connector tube 156 may be integrally formed with the ventilating tube 126, or may be a separate component which is sealed to the ventilating tube 126 by known means.

The dome 130 is formed of a plastics material like that of the tubes 126, 128. The dome 130 is formed at the distal outlet 136b of the ventilating tube 126. The dome 130 has a ramped surface 140 which connects to the intubating tube 128 to act as a ramp for the insertion of the endotracheal tube 24 into the throat of the patient 22 as described herein. The perimeter 131 of the dome 130 distal from the distal ends of the tubes 126, 128 generally forms an ellipse.

The inflatable cuff 132 surrounds the perimeter 131 of the dome 130. A central opening 142 is formed by the cuff 132. The inner edge of the cuff 132 is bonded or otherwise suitably secured, such as by ultrasonic welding, to the perimeter 131 of the dome 130. Thus the inner edge of the cuff 132 is generally elliptical. The cuff 132 is preferably formed of a thin, flexible plastics material so that the cuff 132 can be deflated to a low profile for insertion into the patient's throat and can be inflated once properly positioned to seal with the surrounding tissue when the airway device 120 is correctly positioned in the throat of the patient 22 as described herein.

The centerlines 136d, 138d of the tubes 126, 128 generally fall along the major axis 31f of the ellipse and are offset from each other. As schematically shown in FIG. 10, the distal open outlet 136b of the ventilating tube 126 generally aligns with both foci 31a, 31b as this ventilating tube 126 is large. The distal open outlet 138b of the intubating tube 128 generally aligns with one focus 31b. The ramped surface 140 is between distal open outlet 136b of the ventilating tube 128 and the vertex 31d of the ellipse. The intubating tube 128 and the ramped surface 140 form an intubating passageway.

The airway device 120 includes an inflation line (not shown in FIG. 8) and therefore, the specifics are not repeated herein. Like elements are denoted by like reference numerals with the elements of the second embodiment being denoted with reference numerals in the one-hundreds.

A cap 148 attaches to the proximal inlet 136a of the ventilating tube 126 to prevent access to the open proximal inlet 138a of the intubating tube 128 when the endotracheal tube 24 is not being used. Preferably, the cap 148 is formed of rubber. The cap 148 can have a flip-top as shown to allow access to the intubating passageway 138c, or can be removed from the ventilating tube 126 to allow access to the intubating passageway 138c. Other means for sealing the end of the ventilating tube 126, while selectively allowing access to the intubating passageway 138c, are within the scope of the present invention.

The airway device 120 includes a transmission lumen 168 like that of the first embodiment for transmitting breath and heartbeat sounds from the patient 22 to the medical professional. Therefore, the specifics of the transmission lumen 168 are not repeated herein; like elements are denoted by like reference numerals with the elements of the second embodiment being denoted with reference numerals in the one-hundreds. The transmission lumen 168 seats against the ventilating tube 126 and the distal end of the transmission lumen 168 is either attached to the cuff 132 or is attached near the distal outlet 138b of the ventilating tube 126 near the cuff 132. When the airway device 120 is seated in the throat of the patient 22, the distal end of the transmission lumen 168 is positioned closest to the esophagus which enables breath and heartbeat sounds to be easily transmitted through the perforations 170 and along the length of the transmission lumen 168 to the medical professional monitoring the patient 22.

Like that of the first embodiment, the airway device 120 includes a camera lumen 158 for housing a camera 166. The specifics of these items are not repeated, but like elements are denoted by like reference numerals in the one-hundreds. The distal end of the camera lumen 158 is preferably provided at the vertex 31e of the ellipse between the ventilating tube 126 and the cuff 132 which are sealed thereto. Alternatively, an extruded small-bore lumen can be provided within the wall of the ventilating tube 126, with the window 160 sealed to the end thereof. The camera 166 is preferably provided at the vertex 31e of the ellipse between the ventilating tube 126 and the cuff 132 as this provides the best angle for viewing the tissues of the patient 22 when the airway device 120 is being inserted. It is to be understood that the camera 166 and camera lumen 158 can be placed in other positions.

In both the first and second embodiments of the airway device 20, 120, the camera 66, 166 can be easily slid into and removed from the sealed camera lumen 58, 158. As a result, the camera 66, 166, which is an expensive component, can be used in multiple different airway devices 20, 120 (or other airway devices which have such a sealed camera lumen) by removing it from one airway device and inserting it into another airway device. Since the camera lumen 58, 158 is sealed, it is not necessary to sterilize the camera 66, 166 between uses.

In use, the medical professional inserts the airway device 120 through the mouth and into the throat of the patient 22. The open ventilating tube 126 allows the patient 22 to breathe on his/her own through the connector 156 attached to the ventilating tube 126. The ventilating tube 126 can also be connected to the ventilator 23 to provide assisted breathing to the patient 22. The cuff 132 and the ventilating tube 126 slide against the hard palate and then against the soft palate and into the pharynx of the patient 22. The airway device 20 will flex to assume a curved shape to conform to the throat of the patient 22. The medical professional uses the camera 166 to properly guide the airway device 120 into the pharynx. Because the camera 166 provides constant visualization of the tissues during insertion and the entire time that the airway device 120 is in the patient 22, the medical professional can be assured that the airway device 120 is being properly inserted and maintained. The medical professional can see the vocal folds via the camera 166 to ensure proper positioning of the airway device 120 in the patient's throat. Since the camera 166 is constantly operating, the medical professional can constantly visually confirm movement of the vocal folds to be assured that the patient 22 is breathing. Once positioned in the pharynx, the proximal end of the cuff 132 seats against the epiglottis 74 pushing it toward the tongue 76 of the patient 22 and the distal end of the cuff 132 seats in the esophagus 80. The cuff 132 is then inflated. As a result, the esophagus 80 is blocked by the cuff 132 and the epiglottis 74 is moved out of the way of the ventilating and intubating passageways 136c, 138c. The distal outlets 136b, 138b of the intubating tube 126 and the ventilating tube 128 are open to the glottis of the patient 22. During this entire procedure, the camera 166 provides constant visualization of the tissues during insertion of the airway device 120 into the patient 22 and continues throughout the entire medical procedure. The constant visualization of the laryngeal inlet and the vocal folds of the patient 22 can make earlier diagnoses of issues, for example, but not limited to, secretions, tumors, paralyzed vocal folds, apnea, bleeding, and abnormal anatomy, as well as other potentially harmful effects to the patient 22.

The patient can breathe by airflow through the connector 156/ventilating tube 126. Air can also flow through the slit 152 and through the intubating tube 128 to the patient 22.

If the medical professional needs to insert an endotracheal tube 24 into the patient 22, the cap 148 is removed/opened (opened via removing the plug 148a on the cap 148 to open the passageway 148b in the cap 148) to allow access to the proximal inlet 138a of the intubating tube 128 and the endotracheal tube 24 is inserted through the proximal inlet 138a and through the intubating passageway 138c. The endotracheal tube 24 will contact the ramped surface 140 which properly directs the endotracheal tube 24 into the pharynx. Once the endotracheal tube 24 exits the intubating tube 28, the medical professional can see the positioning of the endotracheal tube 24 via the camera 166. The medical professional can thus guide the endotracheal tube 24 through the vocal folds and into the trachea, and then inflate the cuff of the endotracheal tube 24, under the constant visualization provided by the camera 166. At times, the airway device 120 may be advanced, pulled back, or turned from side to side, to maintain the proper trajectory through the vocal folds. In addition, known moveable stylettes (not shown) may be used. The ventilator 23 is then disconnected from the ventilating tube 26 and the connector 156 may be capped (although it can be left open since the endotracheal tube 24 is in place), or the ventilator 23 can remain connected, but turned off.

Figure 9A:
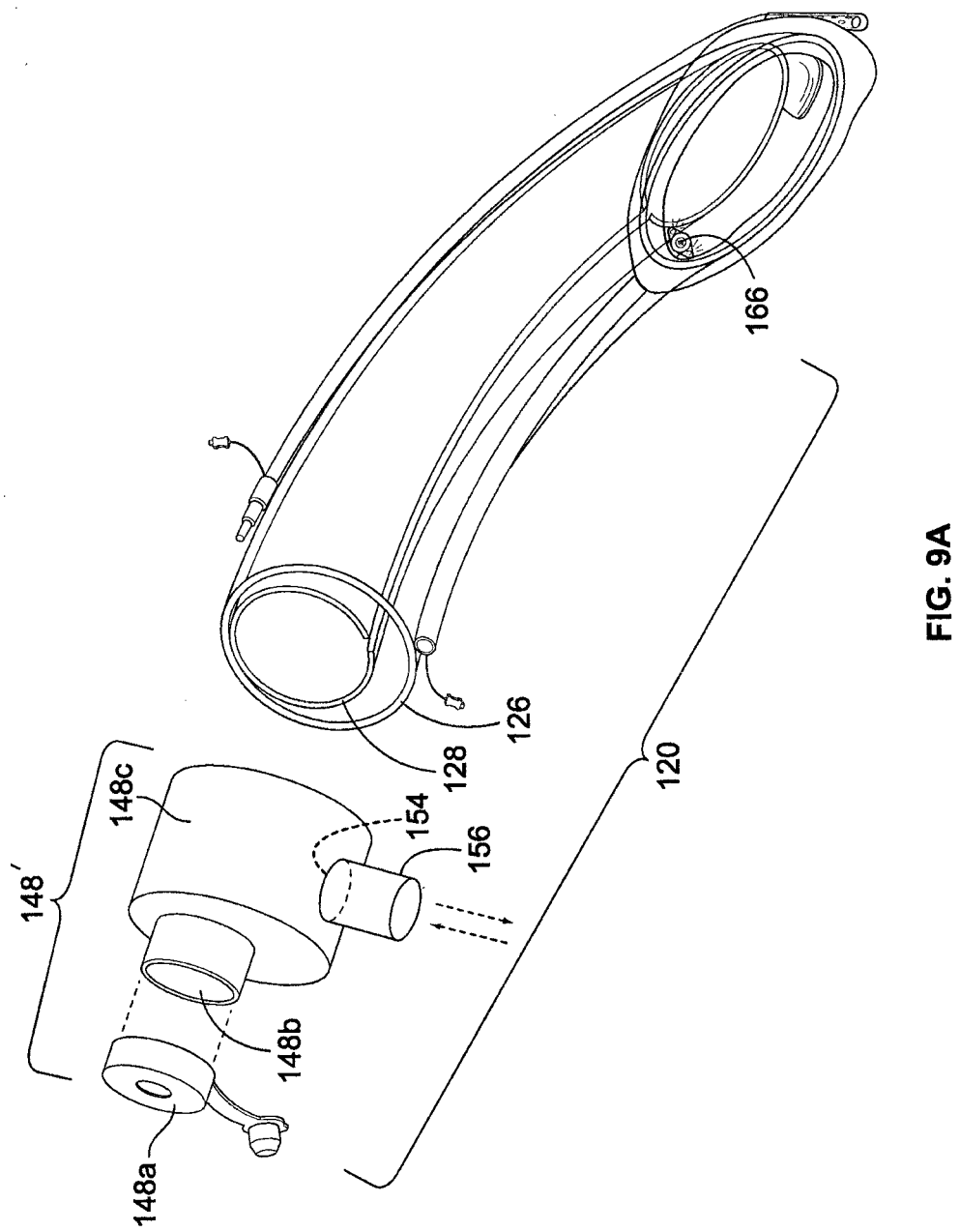
FIG. 9A is a perspective view of a modification to the airway device of FIG. 9.

In this embodiment of the airway device 20, the ventilating port 154 and connector tube 156 can be moved from the tube 126 to a modified cap 148' as shown in FIG. 9A (like that of FIG. 9, tube 128 is shown in full line in FIG. 9A to illustrate the construction of the tube 128 (of course, in practice, tube 126 may be opaque such that tube 128 would not be visible along its length)). This modified cap 148' allows for ventilation (via ventilation port 156/connector tube 154), intubation (intubation is achieved by removing the plug 148a on the cap 148' to open the passageway 148b in the cap 148'), and connection to the tube 128. The skirt 148c of the cap 148 is longer than the skirt of the cap 148 to accommodate the ventilation port 156, while still allowing the cap 148' to be connected to the tube 128.

The intubating tube 128 is located furthest away from the epiglottis 74 when the airway device 120 is inserted. This minimizes the ability of the epiglottis 74 to block the insertion of the endotracheal tube 24 into the trachea of the patient 22 in the event that the epiglottis 74 is not seated between the cuff 132 and the tongue 76.

The dual tubes 26/126, 28/128 thus provide the ability for a patient 22 to breathe on his/her own, to breathe under ventilation via the ventilator 23, or to be intubated using the endotracheal tube 24. The endotracheal tube 24 can be removed from the intubating tube 28, 128 and the intubating tube 28, 128 capped, and the patient 22 can return to breathing on his/her own or under ventilation through the ventilating tube 26, 126 without removal of the airway device 20, 120 from the patient 22. If the patient 22 becomes distressed or if circumstances dictate, the endotracheal tube 24 can be reinserted into the intubating tube 28, 128. This provides great flexibility for the medical professional to keep the patient's airway open, to constantly visually verify that the patient's airway is open during the entire medical procedure, and to constantly verify by hearing that the patient's airway is open during the entire procedure.

The transmission lumen 68, 168 is positioned proximate to the esophagus 80 which is the location closest to the lungs and heart of the patient 22. This enables breath and heart sounds to be easily transmitted along the transmission lumen 68, 168.

Figure 11:
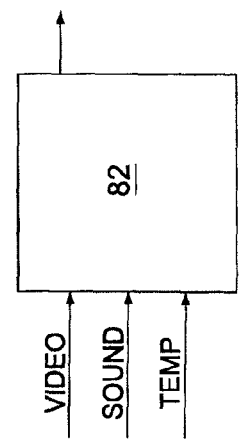
FIG. 11 is a schematic of a control system for use with the airway devices of FIGS. 1 and 9/10.
Figure 12:
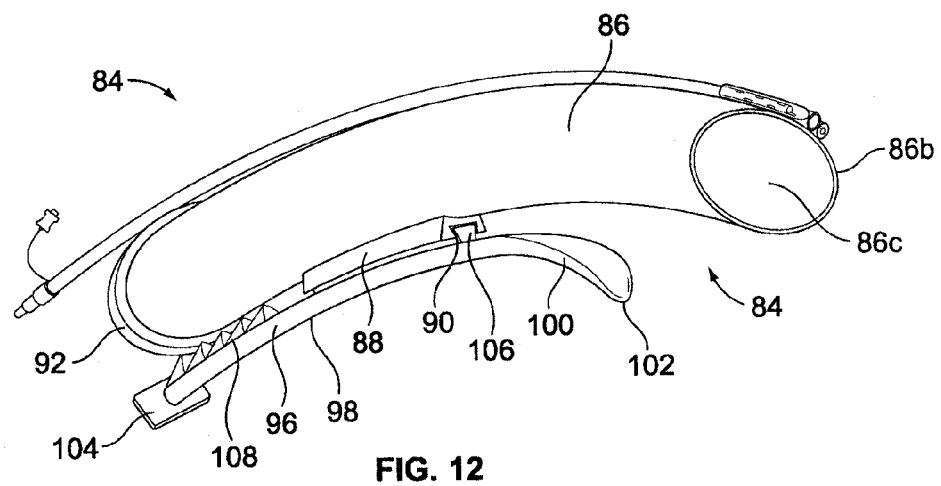
FIG. 12 is a perspective view of an airway assist device for use with the airway devices of FIGS. 1 and 9/10.
Figure 13:
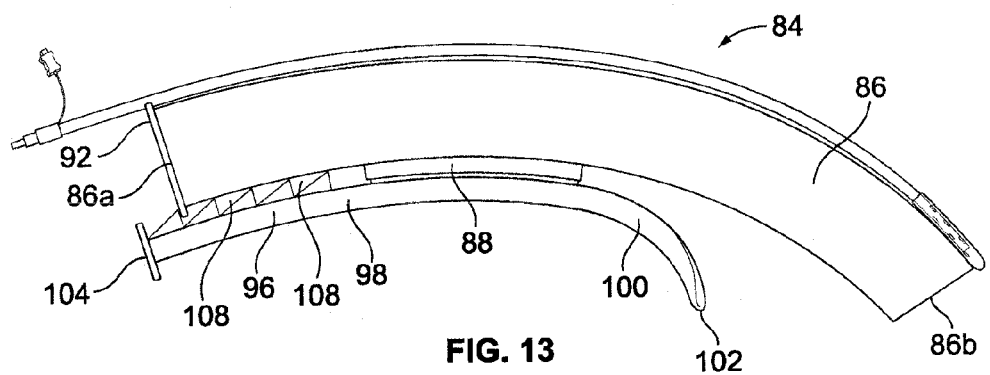
FIG. 13 is a side elevational view of the airway assist device.
Figure 14:
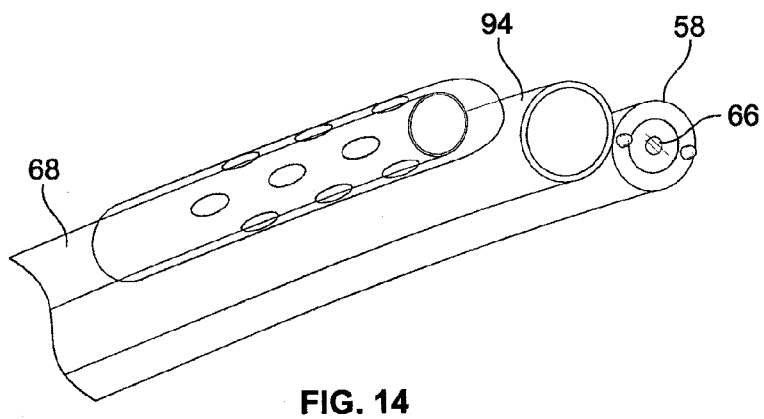
FIG. 14 is a perspective view of the lumens which form part of the airway assist device.
Figure 15:
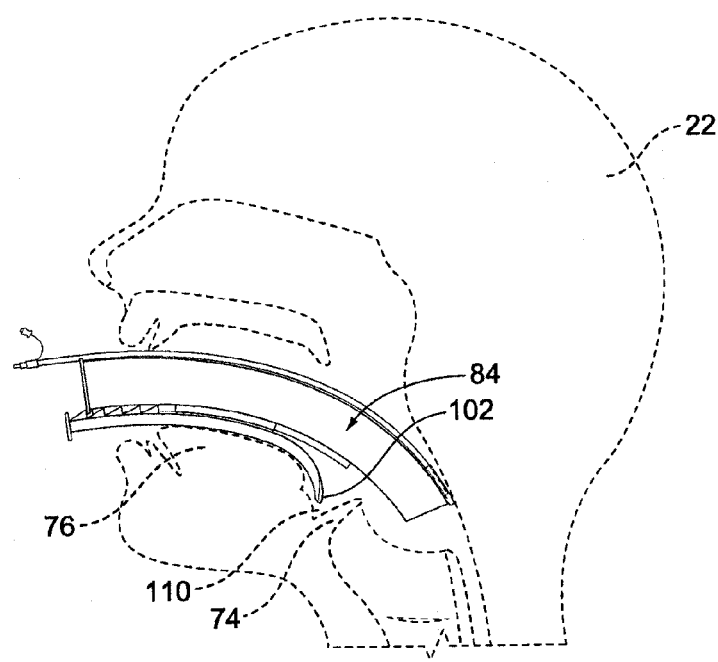
FIGS. 15 and 16 are side elevational views of the airway assist device inserted into a patient.
Figure 16:
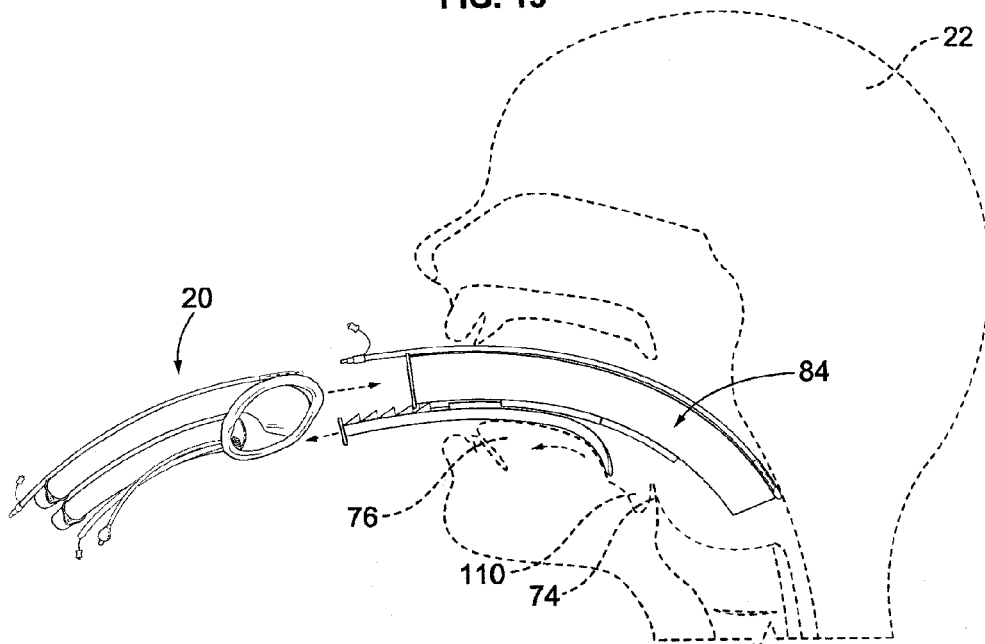
Figures 17, 18:
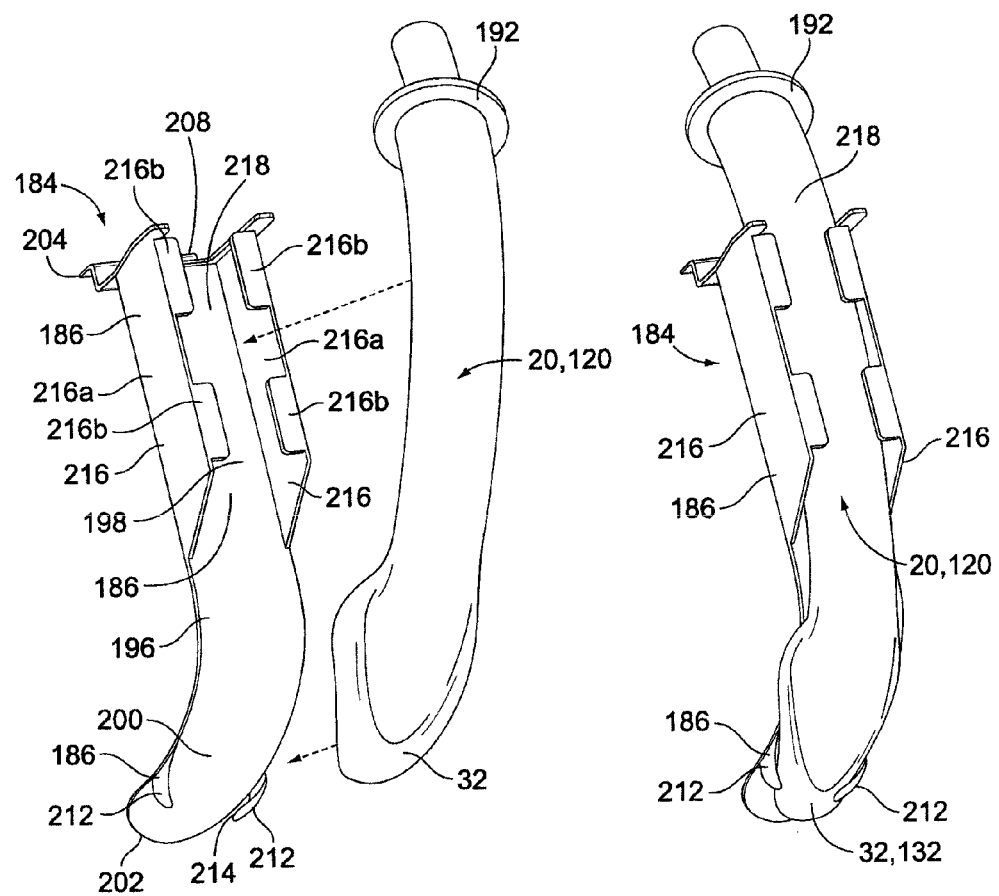
FIG. 17 is a perspective view of an alternate airway assist device for use with the airway devices of FIGS. 1 and 9/10.
FIG. 18 is a perspective view of the airway assist device of FIG. 17 with an airway device mounted therein.
Figure 19:
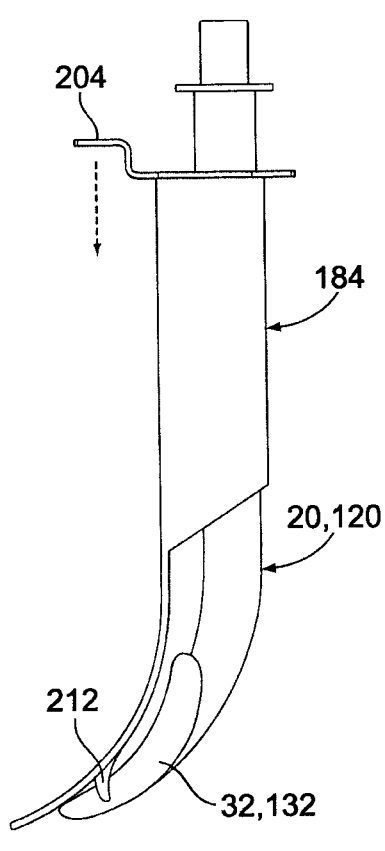
FIGS. 19 and 20 are side elevational views of the airway assist device of FIG. 17 with an airway device mounted therein.
Figure 20:
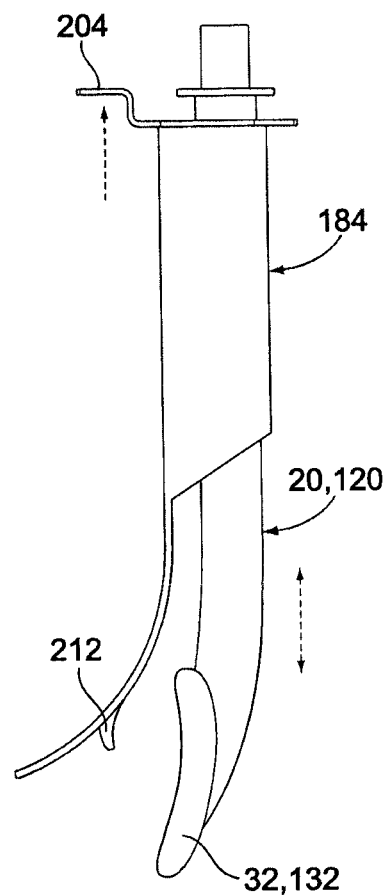

The airway device 20, 120 is intended to be in the patient 22 during the entire medical procedure. The video information from the camera 66, 166 and the information from the transmission tube 68, 168 are transmitted to a microprocessor 82, FIG. 11, via appropriate means, such as wires, wireless, Bluetooth, etc., which in turn can transmit the information to another computer, mobile devices, a mobile station and the like, via appropriate means, such as wires, wireless, Bluetooth, etc., and then this information can be accessed by appropriate personnel. This microprocessor 82 can be on-site where the procedure is being performed or can be remote from the procedure site. For example, the information can be supplied to the nurses' station and the nurse on duty will be able to instantly know if the patient 22 is breathing by the visual confirmation that the vocal folds are opening and closing and by hearing breath and heart sounds. The medical professional will be able to interpret the depth of anesthesia by looking at the rhythmic movement of the vocal folds as well as other diagnoses previously mentioned. Other medical personnel can be hundreds of miles away and still be able to monitor, advise, confirm, and diagnose without the patient 22 being in close physical proximity to that medical personnel. Since the camera 66, 166 is constantly operating, medical personnel can tell at any time if the patient 22 is properly ventilated/intubated and is breathing.

If desired, the airway device 20, 120 can be removed once the endotracheal tube 24 is properly positioned because the intubating passageway 38c, 138c is sufficiently large to slide over the endotracheal tube 24 without dislodging the endotracheal tube 24 from the patient's throat.

A temperature sensor can also be incorporated into the airway device 20, 120 for providing temperature information to the appropriate personnel via the microprocessor 82.

The airway device 20, 120 is disposable. Since the camera 66, 166 can be removed from the airway device 20, 120, an expensive component of the airway device 20, 120 is reusable. While the lights 62, 162 are described as being provided in the airway device 20, 120, it is possible for the lights 62, 162 to be built into the camera 66, 166.

FIGS. 12-16 show a first embodiment of an airway assist device 84 and FIGS. 17-20 show a second embodiment of an airway assist device 184, each of which are used in combination with the airway device 20, 120. The airway assist device 84, 184 can be used to manipulate the position of the patient's epiglottis 74 and tongue 76 to further ensure that the epiglottis 74 and tongue 76 are moved out of the way of the ventilating and intubating passageways 36c, 136c, 38c, 138c and to minimize the chance of blockage of the passageways 36c, 136c, 38c, 138c by the epiglottis 74. These airway assist devices 84, 184 allow first responders, for example, paramedics, an easier way to provide patency to the airway of the patient 22, and to easily advance the airway device 20, 120 under constant visualization by the camera 66, 166.

Attention is invited to the airway assist device 84 shown in FIGS. 12-16. The airway assist device 84 is formed from an airway holder 86 and a tongue positioner 96.

The airway holder 86 is formed of a cylindrical tube which has a central passageway 86c extending from a proximal end 86a thereof to a distal end 86b thereof. The central passageway 86c has a large enough diameter to allow the airway device 20, 120 to pass therethrough. The airway holder 86 is preferably curved in the same shape as the airway devices 20, 120.

An elongated mounting extension 88 extends from the airway holder 86. The mounting extension 88 has a dovetail opening 90 extending along the length thereof. Alternatively, the wall of the airway holder 86 could be thickened and the dovetail opening 90 formed therein. A collar 92 is provided at the proximal end 86a of the airway holder 86 and extends perpendicularly therefrom.

The airway assist device 84 includes a camera lumen 58 for housing a camera 66 and a transmission lumen 68 attached to the outer surface of the airway holder 86 at a position which is diametrically opposed to the mounting extension 88. The camera lumen 58, the camera 66 and the transmission lumen 68 are identical to those shown in the airway devices 20, 120 and the specifics are therefore not repeated. A lumen 94 for housing a temperature sensor is also provided (such a lumen 94 and temperature can be provided with the airway devices 20, 120). As shown, the lumens 58, 68, 94 are positioned side-by-side and attached to the airway holder 86 by suitable means. The lumens 58, 68, 94 can be integrally formed with the airway holder 86.

The tongue positioner 96 is slidably received in the mounting extension 88. The tongue positioner 96 has an elongated body 98 which is curved and has a distal end 100 which has a radius which is substantially greater than the radius at which the body 98 is curved. The edge 102 of the distal end 100 is preferably arcuate. A handle 104 is provided at the proximal end of the body 98 which enables a medical professional to grasp the tongue positioner 96. The tongue positioner 96 is preferably formed of a rigid plastic. The distal end 100 may be covered with a soft material, such as silicone. A dovetail protrusion 106 extends outwardly from the body 98 and seats within the dovetail slot 90 in the mounting extension 88.

A series of spaced apart ratchet teeth 108 extend outwardly from the body 98 proximate to the handle 104. The teeth 108 are capable of engaging with the collar 92 to hold the position of the tongue positioner 96 proximally and distally relative to the airway holder 86.

In use, the medical professional inserts the airway assist device 84 into the mouth of the patient 22. The airway holder 86/lumens 58, 68, 94 slide against the hard palate and then against the soft palate and partially into the pharynx of the patient 22 until the distal end 100 of the airway assist device 84 enters into the vallecula 110 and the edge 102 engages the tissues of the patient 22. The tongue positioner 96 may slide along the patient's tongue 76. The camera 66 on the airway assist device 84 allows the medical professional to see the tissues and determine the proper positioning of the airway assist device 84. Once properly positioned in the vallecula 110, the medical professional pulls on the handle 104 to move the tongue positioner 96 proximally relative to the airway device tube 86. The distal end 100 engages the patient's tongue 76 and pulls the tongue 76 proximally toward the outside of the mouth of the patient 22. As a result, the epiglottis 74 is also pulled proximally to further open the airway of the patient 22. The teeth 108 ratchet on the collar 92 of the airway holder 86 and prevent the tongue positioner 96 from moving distally relative to the airway holder 86. During this procedure, the patient 22 can breathe through the central passageway 86c of the airway holder 86.

When the epiglottis 74 is pulled proximally, the medical professional inserts the airway device 20, 120 into the central passageway 86c of the airway assist device 84 and properly positions the airway device 20, 120 in the patient's throat as described herein. After insertion of the airway device 20, 120, the medical professional releases the patient's tongue 76 by pulling the tongue positioner 96 away from the airway holder 86 to disengage the teeth 108 from the collar 92. The rigid plastic of the tongue positioner 96 has enough flexibility to allow the elastic deformation of the tongue positioner 96. Once the teeth 108 are disengaged from the collar 92, the medical professional pushes the tongue positioner 96 distally relative to the airway holder 86 to cause the tongue 76 of the patient to move rearwardly into the patient's mouth. Thereafter, the airway assist device 84 can be removed from the patient's mouth by sliding it over the airway device 20, 120.

Attention is invited to the airway assist device 184 shown in FIGS. 17-20. With this embodiment, the ventilating tube 26, 126 has a collar 192 at its proximal end which extends perpendicularly from the ventilating tube 26, 126.

The airway assist device 184 includes a tongue positioner 196 having an elongated body 198 which is curved and has a distal end 200 which has a radius which is substantially greater than the radius at which the body 198 is curved. The edge 202 of the distal end 200 is preferably arcuate. A handle 204 is provided at the proximal end of the body 198 which enables a medical professional to grasp the tongue positioner 196. The tongue positioner 196 is preferably formed of a rigid plastic. The distal end 200 may be covered with a soft material, such as silicone.

The airway holder 186 includes a pair of tabs 212 and a pair of arms 216.

The tabs 212 extend upwardly from the distal end 200 proximate to, but spaced from, the edge 202. Each tab 212 is curved and aligned with each other such that the ends of the tabs 212 face each other. As a result, a space 214 is formed between each of the tabs 212 and the distal end 200. This space 214 has a dimension which is approximately equal to the inflatable cuff 32, 132 in the deflated condition. The tabs 212 are spaced apart from each other a distance which is generally equal to the width of the inflatable cuff 32, 132.

The arms 216 extend upwardly from the body 198. Each arm 216 is generally L-shaped, with a first section 216a extending perpendicularly from the body 198 and second sections 216b extending perpendicularly from the first section 216a. The ends of the second sections 216b are spaced apart from each other to form a slot 218. The slot 218 has a width which is slightly less than the diameter of the airway device 20, 120. The arms 216 and the body 198 form an airway device receiving passageway 186.

A tooth 208 extends upwardly from the proximal end of the body 198 between the arms 216. The tooth 208 is capable of engaging with the collar 192.

In use, the medical professional first inserts the airway device 20, 120 into the airway assist device 184 by inserting the airway device 20, 120 through the slot 218 and into the central passageway 186 of the airway assist device 184. The arms 216 can elastically flex outwardly as necessary to allow the airway device 20, 120 to pass through the slot 218. The cuff 32, 132 seats underneath the tabs 212 such that the cuff 32, 132 is sandwiched between the tabs 212 and the distal end 200.

The medical professional then inserts the combined airway device 20, 120/airway assist device 184 into the mouth of the patient 22. The airway assist device 184 is sandwiched between the airway device 20, 120 and the tongue 76 of the patient 22. The airway device 20, 120 slides against the hard palate and then against the soft palate and partially into the pharynx of the patient 22 until the distal end 100 of the airway assist device 84 enters into the vallecula 110 and the arcuate edge 202 engages the tissues of the patient 22. The camera 66, 166 on the airway device 20, 120 provides visual means to the medical professional to properly insert the distal end 200 into the vallecula 110. The tongue positioner 196 may slide along the patient's tongue 76. Once the distal end 200 is positioned in the vallecula 110, the medical professional pulls on the handle 204 to move the tongue positioner 196 proximally relative to the airway device 20, 120. The distal end 200 engages the tongue 76 and pulls the tongue 76 proximally toward the outside of the mouth of the patient 22. As a result, the epiglottis 74 is also pulled proximally. During this procedure, the patient 22 can breathe through the airway device 20, 120 as described herein.

When the epiglottis 74 is pulled proximally, the medical professional then pulls the airway device 20, 120 proximally to release the cuff 32, 132 from the tabs 212. The freed airway device 20, 120 then can be finally inserted with the distal end of the airway device 20, 120 in the upper esophagus of the patient 22 as discussed above.

After insertion of the airway device 20, 120, the medical professional releases the patient's tongue 76 by pushing the tongue positioner 196 distally into the patient's mouth to cause the tongue 76 of the patient to move rearwardly. Thereafter, the airway assist device 184 can be removed from the patient's mouth by sliding it over the airway device 20, 120.

While the cuff 32, 132 has been described as inflatable, the cuff 32, 132 can be formed of a soft material, such as silicone, which will readily seal with the tissues in the glottis when the airway device 20, 120 is seated therein.

While preferred embodiments of the present invention are shown and described, it is envisioned that those skilled in the art may devise various modifications of the present invention without departing from the spirit and scope of the appended claims.

What is claimed is:

1. An airway device capable of insertion into the throat of a patient to open the airway of the patient, said airway device comprising:
    a dome having a generally elliptical perimeter defining a major axis and pair of vertices;
    a ventilating tube formed of a compliant plastics material, said ventilating tube having a proximal end and an opposite distal end, a ventilating passageway extending from said proximal end to said distal end, said ventilating passageway terminating in a ventilating outlet at said distal end thereof, the ventilating outlet emptying into the dome;
    an intubating tube formed of a compliant plastics material, said intubating tube having a proximal end and an opposite distal end, an intubating passageway extending from said proximal end to said distal end, said intubating passageway terminating in an intubating outlet at said distal end thereof, the intubating outlet emptying into the dome;
    said ventilating tube and said intubating tube are positioned side-by-side such that said ventilating outlet and said intubating outlet intersect said major axis; and
    wherein said ventilating tube is adapted to be connected to a ventilator capable of ventilating the patient, and said intubating tube is capable of receiving an endotracheal tube therethrough.

2. The airway device of claim 1, further comprising a ramp provided by said dome at said distal end of said intubating tube.

3. The airway device of claim 1, further comprising a cuff surrounding said perimeter of said dome.

4. The airway device of claim 3, wherein said cuff is inflatable, and further comprising an inflatable line attached to said cuff capable of inflating said cuff.

5. The airway device of claim 1, further comprising a camera attached to said dome.

6. The airway device of claim 5, wherein said camera is proximate to one of the vertices.

7. The airway device of claim 5, further comprising a camera lumen attached to said dome, wherein said camera is insertable and removeable from said camera lumen.

8. The airway device of claim 7, wherein said dome has at least one light which is proximate to said camera lumen.

9. The airway device of claim 1, further including a transmission lumen attached to said dome, said transmission lumen including a plurality of perforations and a cap covering said perforations, said transmission lumen capable of transmitting heart and breath sounds to a medical professional.

10. The airway device of claim 7, wherein a distal end of the camera lumen which is proximate to the dome has a clear window provided thereon which seals the distal end of the camera lumen.

11. The airway device of claim 1, further comprising a cap mounted at the proximal end of the intubating tube capable of selectively sealing the proximal end of the intubating tube.

12. The airway device of claim 1, wherein the distal ends of the ventilating and intubating tubes are generally aligned with each other.

13. An airway assist device used in combination with the airway device of claim 1, wherein said airway assist device comprises:
    an elongated, curved, rigid body having a proximal and a distal end, said distal end of said body being curved at a greater radius than the remainder of the body, said distal end being insertable into the vallecula of a patient;
    a handle at said proximal end of said body, wherein a medical professional can grasp the handle and pull the tongue of the patient proximally toward the front of the mouth of the patient when the distal end of the body is positioned within the vallecula;
    a tube into which the airway device is seated, the tube of said airway assist device being moveably attached to the body.

14. The airway assist device and airway device combination of claim 13, wherein said airway assist device further includes a plurality of teeth on one of said body and said tube, the plurality of teeth on one of said body and said tube engaging a protrusion on the other of said body and said tube, said teeth engaging said protrusion to maintain the positions of said tube and said body relative to each other.

15. The airway assist device and airway device combination of claim 13, wherein the body is non-tubular.

16. The airway assist device and airway device combination of claim 13, wherein the tube has an external surface and an internal surface which defines a passageway through which the airway device is seated; and the body is attached to the external surface of the tube.

17. An airway device capable of insertion into the throat of a patient to open the airway of the patient, said airway device comprising:
    a ventilating tube formed of a compliant plastics material, said ventilating tube having a proximal end and an opposite distal end, a ventilating passageway extending from said proximal end to said distal end and a centerline defined along said ventilating passageway between said proximal and distal ends, said ventilating passageway terminating in a ventilating outlet at said distal end thereof;
    an intubating tube formed of a compliant plastics material, said intubating tube having a proximal end and an opposite distal end, an intubating passageway extending from said proximal end to said distal end and a centerline defined along said intubating passageway between said proximal and distal ends, said intubating passageway terminating in an intubating outlet at said distal end thereof;
    said distal ends of said tubes being generally aligned with each other;

a dome provided at said distal ends of said tubes such that the distal ends of the ventilating and intubating tubes empty into the dome, said dome having a generally elliptical perimeter defining a major axis and a pair of vertices;

said centerlines of said ventilating and intubating tubes generally falling along said major axis;

wherein said ventilating tube is adapted to be connected to a ventilator capable of ventilating the patient, and said intubating tube is capable of receiving an endotracheal tube therethrough;

a camera lumen attached to said dome, said camera lumen having an end provided proximate to one of the vertices of said perimeter of said dome;

a camera insertable and removeable from said camera lumen; and a transmission lumen attached to said dome, said transmission lumen including a plurality of perforations and a cap covering said perforations, said transmission lumen capable of transmitting heart and breath sounds to a medical professional.

18. The airway device of claim 17, further comprising a clear window provided at the end of the camera lumen, the clear window sealing the end of the camera lumen.

19. The airway device of claim 17, further comprising a cap mounted at the proximal end of the intubating tube capable of selectively sealing the proximal end of the intubating tube.

20. The airway device of claim 17, further comprising a cuff surrounding the perimeter of the dome.

21. The airway device of claim 20, wherein the cuff is inflatable, and further comprising an inflatable line attached to the cuff capable of inflating the cuff.

* * * * *